United States Patent
Perichon et al.

(10) Patent No.: US 6,906,214 B2
(45) Date of Patent: Jun. 14, 2005

(54) PREPARATION OF AROMATIC ORGANOZINC COMPOUNDS AND COMPOSITION THEREFORE

(75) Inventors: Jacques Perichon, Savigny-sur-Orge (FR); Corinne Gosmini, Savigny-sur-Orge (FR); Hyacinthe Fillon, Thiais (FR)

(73) Assignee: Rhodia Chimie, Boulogne Billancourt (FR)

( * ) Notice: Subject to any disclaimer, the term of this patent is extended or adjusted under 35 U.S.C. 154(b) by 0 days.

(21) Appl. No.: 10/482,319

(22) PCT Filed: Jul. 3, 2002

(86) PCT No.: PCT/FR02/02319

§ 371 (c)(1),
(2), (4) Date: Jun. 18, 2004

(87) PCT Pub. No.: WO03/004504

PCT Pub. Date: Jan. 16, 2003

(65) Prior Publication Data

US 2004/0236155 A1 Nov. 25, 2004

(30) Foreign Application Priority Data

Jul. 4, 2001 (FR) .......................................... 01 08880

(51) Int. Cl.⁷ .............................. C07F 3/06; C09K 3/00
(52) U.S. Cl. ................... 556/128; 556/121; 252/183.14
(58) Field of Search ................ 556/121, 128; 252/183.14

(56) References Cited

U.S. PATENT DOCUMENTS

| | | | |
|---|---|---|---|
| 6,211,380 B1 * | 4/2001 | Fantucci et al. | 548/101 |
| 6,258,967 B1 * | 7/2001 | Blacker et al. | 556/121 |
| 6,521,771 B2 * | 2/2003 | Frommeyer et al. | 556/121 |
| 6,808,655 B1 * | 10/2004 | Perichon et al. | 252/519.2 |

FOREIGN PATENT DOCUMENTS

| | | | |
|---|---|---|---|
| EP | 0 494 419 | 7/1992 | C07C/65/05 |
| WO | WO 01/02625 | 1/2001 | C25B/3/12 |

OTHER PUBLICATIONS

Fillon, H et al; Tetrahedron Letters (2001), 42(23), 3843–3846, XP004240102 The whole document.

Gosmini, Corinne et al ; Journal of Organic Chemistry (2000), 65(19), 6024–6026, XP002195474 the whole document.

Buriez, O et al. ; Journal of Electroanalytical Chemistry (2001), 506(2), 162–169, XP002195473 the whole document.

International Search Report (2002).

* cited by examiner

*Primary Examiner*—Porfirio Nazario-Gonzalez

(57) ABSTRACT

The invention relates to a technique for preparing aromatic organozinc compounds and to a composition therefore. This composition constitutes a reactant that can be used to carry out the synthesis of organozinc compounds, and comprises a cobalt salt, a zinc salt, a polar aprotic solvent and elemental zinc in divided form, the elemental zinc being in solid form, the other elements being in a form dissolved in the solvent. Application to organic synthesis.

10 Claims, No Drawings

PREPARATION OF AROMATIC ORGANOZINC COMPOUNDS AND COMPOSITION THEREFORE

This application is an application under 35 U.S.C. Section 371 of International Application Number PCT/FR02/02319 filed on Jul. 3, 2002.

The subject of the present invention is a novel method of synthesizing aryl organozinc derivatives. It relates more particularly to the synthesis of aryl organozinc derivatives by a chemical route in the catalytic presence of the element cobalt.

The reactivity of organozinc compounds, especially aryl organozinc compounds, has many specific features that make them particularly useful in many organic synthesis operations. However, they are difficult to obtain and are often prepared from organometallic compounds produced with more electronegative, that is to say more reducing, metals.

Furthermore, most of the techniques require the use of highly aprotic, and especially very dry, media.

Important advances have been recently made by the same authors as those of the present application, which advances have formed the subject of the patent application published by virtue of the patent cooperation treaty under number WO 01/02625 A1. The technique described in that patent proposes an electrolytic synthesis in the presence of zinc salts and in the presence of cobalt salts. The cathodic reduction of the system results in the synthesis of organozinc compounds with good coulumbic yields. This technique is also very versatile. In this technique, metallic zinc possibly present at the anode acts only as a source of zinc salt, the reaction taking place at the cathode.

However, this technique has the drawbacks associated with any electrolysis.

Thus, it is relatively expensive to implement such a technique, and an electrolytic technique can be applied only to expensive products.

Another problem lies in the difficulty in producing large amounts in small volumes by electrolytic techniques.

One of the objectives of the present invention is therefore to provide a method for obtaining organozinc derivatives with good yields, both reaction and conversion yields, and to do so without using an electrolytic technique. These objectives, and others that will appear later, are achieved by the use of cobalt as catalyst for the reaction between metallic zinc and an aryl halogen, and to do so without an electrolysis device.

Thus the particle, or fragment taken in its entirety, of zinc is not connected to any external electrolytic system, that is to say one in which the current source is located outside the reaction mixture, which therefore does not have the right to be called an "electrolytic bath" and does not act as anode. The formation of an organozinc compound may be termed chemical formation as no apparent current can be detected.

It will be assumed that one day an electrochemical mechanism will be assigned to this reaction; the same parcel of metal will then act at the same time as cathode and as anode.

This chemical nature of the reaction is demonstrated by the divided form of the introduction of the metal—the zinc is introduced in divided form, for example powder, machining chips, shot, etc. and is brought into contact with no current source. There is no electrical connection between the zinc and a current source external to the medium, which is consequently not an "electrolytic" medium but simply a reaction mixture.

Over the course of the study that led to the present invention, it was shown that it is preferable to avoid the use of good cobalt complexing agents, and especially bidentate complexing agents such as bipyridyls. Pyridine itself considerably slows down the reaction, favoring side reactions.

On the other hand, light complexing agents, such as nitrile and possibly dinitrile functional groups, seem to favor the reaction.

Thus, according to the present invention, it is preferable that the complexing agents of pyridinic type be less than two times, preferably less than one times, the amount expressed in moles of cobalt salts.

It is desirable for the same rules to apply to the strong cobalt complexing agents, such as optimally bidentate amines and phosphines.

This rule may be expressed in the following manner: the high molar ratio of cobalt to coordinating ligand, chosen from pyridines, phosphines and amines, is greater than 0.5, advantageously equal to 1 and preferably 2.

When a complexant is multidentate, the above rule will apply using the equivalents of complexing function and not the number of moles of complexing product function.

It has also been shown that the presence of an aryl halide can potentialize the reaction, especially when the ring carrying the X of said ArX is at least as rich in electrons as a phenyl. This potentialization is most particularly effected by means of aryl halides of a ring less rich in electrons than that of ArX, the zinc compound of which it is desired to produce.

To evaluate the electron richness of a ring, reference may be made to the Hammett constants taking as reference the Hammett constant $\sigma_p$. This catalysis of the zinc by cobalt is surprising insofar as, usually, zinc is capable of reducing in metallic form, by a technique sometimes called cementation, the element cobalt, which is less reducing than zinc.

According to another aspect of the invention, it has also been shown that the presence of acid, advantageously an organosoluble acid, significantly improves the yields.

These acids may especially be carboxylic acids, fatty acids or halogenated, and even perhalogenated, acids. Perfluorinated acids are of particular interest because of their solubility in organic phases and of their relatively high acidity.

Without this explanation being limiting, it is plausible that the role of these acids is to depassivate the zinc used. The solvents used are preferably solvents of the polar aprotic type, and especially those whose donor number is at least equal to 10 and preferably at most equal to 30, advantageously between 20 and 30, the limits being inclusive.

Said donor number corresponds to the $\Delta H$ (change in enthalpy) expressed in kilocalories per mole of the combination of said polar aprotic solvent with antimony pentachloride. This is described more precisely in the work by Christian Reichardt: "*Solvents and solvent effects in organic chemistry*" VCH, page 19, 1988. On this page is found the definition of the donor number.

With the exception of the particular case of nitrites, it is preferable for the donor character to be due neither to the nitrogen nor to the phosphorus, but instead due to oxygen.

In the case of solvents with amide functional group, it will be assumed that the donor aspect is due to the oxygen linked by a double bond to the carbon of the amide functional group. Thus, amides form part of the solvents capable of giving good results in the case of the reaction according to the invention.

The solvent must be sufficiently polar to dissolve the metals, or more precisely the salts of the metals used, and must be sufficiently lipophilic to at least partly dissolve the substrates of which it is desired to form the organozinc compound. It is preferable to use solvents that are sufficiently scarcely acidic (it is desirable for their pKa to be at least equal to 16, advantageously at least equal to 20 and preferably at least equal to 25) for the reactions with hydrogen to be as scarcely pronounced as possible. Thus, primary alcohols are too acidic to give good results.

If there is need for acidity, it is then necessary to control its amount using the acids that were mentioned above, and especially carboxylic acids such as trifluoroacetic acid and acetic acid itself. Fatty acids may also be used, whether or not they are perhalogenated (in general perfluorentated) on the carbon carrying the carboxylic functional group.

Returning to the solvents, it will be preferable more specifically to use what are called polar aprotic solvents such as, for example, by themselves or as a mixture:

- purely oxygen-type solvents, particularly ethers, preferably polyethers such as 1,2-dimethoxy ethane, or cyclic ethers such as THF or dioxane;
- amides or ureas (DMF, N-methyl-2-pyrrolidone, imidazolidone, tetramethylurea, dimethoxypropylene, etc.);
- sulfones (for example sulfolane) or sulfoxides (such as DMSO). However, it will then be necessary, in these cases too, to check that the zinc is not able, under the reaction conditions, to reduce these solvents;
- compounds with a nitrile functional group (for those that are preferred, see below); and
- nitriles; in order to be used these must preferably be liquid at the reaction temperature (as goes without saying), but polynitriles may also be used, and especially bis-nitriles. These bis-nitriles are of particular interest because they are scarcely complexing. They may be used as solvent, cosolvent or light complexing agent, without lowering the yield.

It is desirable, in order to avoid the medium becoming too acidic, for the bis-nitriles, that constitute the solvent, part of the solvent or the coordinate, to be such that two nitrile functional groups are separated by at least two carbons, advantageously by three carbons, via the most direct path.

Dinitriloalkylenes whose alkylene group contains from 2 to 8 carbon atoms give good results. Mention may be made in particular of glutaronitrile, methylglutaronitrile, adiponitrile, pimelonitrile and suberonitrile.

The cobalt may be introduced into the reaction mixture in various ways and above all in various forms, but it is preferable for it to be introduced in the form of a salt, preferably a cobaltous salt. Cobaltic salts may also be used, but they will cause additional consumption of zinc.

To be effective, it is desirable for the cobalt to be present in a minimum concentration, at least equal to $10^{-3}$M. To be economic, it is preferable for the cobalt not to be too concentrated—therefore the cobalt content is at most equal to 0.2 M. It has been shown during the present study that zinc salts can be useful at start-up of the reaction. It is therefore preferable to add zinc salts to the initial reaction mixture. These zinc salts may be any kind of salt, but it is often more practical to introduce them in the form of a halide, and especially of the halide corresponding to the halides of the substrates of which it is desired to form the organozinc compound.

The same applies to cobalt. However, it is necessary to avoid a multiplicity of anions in the mixture in order to be able more easily to treat the reaction solutions.

There is no clear-cut maximum amount of zinc salts to be used, but it is preferable to arrange for the zinc salt, after the end of the reaction, not to exceed the solubility of said zinc salt in the media.

It is possible to dispense with a zinc salt, but the reaction, in all cases in its starts, will become autocatalytic, the zinc salts being formed during the reaction. It is thus preferable to have a zinc salt concentration of at least $10^{-3}$M, preferably at least $10^{-2}$M.

Aryl halides, that potentialize or act as adjuvant for the reaction, are especially denoted in the examples by Ar'X', where X' represents the halide in question. The amounts of adjuvant halide (Ar'X') may be very low, but it is preferable for them to be at least equal to $10^{-3}$M. It is also preferable for its concentration to be at most equal to, and even less than, that of the cobalt expressed in moles per liter. This is because if it is greater than that of cobalt, organozinc compounds of the adjuvant are present that may constitute an impurity with regard to the desired organozinc compound. X' may take the same values as X (especially chlorine, bromine, iodine), but ordinarily X' is chosen to be equal to X.

When Ar'X' remains less than the amount of cobalt present (expressed in moles per liter), the possible intermediate organozinc compound is essentially converted into a hydrogenated derivative corresponding to the adjuvant aryl halide.

When the adjuvant aryl halide is such that the halogen is close (in the ortho or equivalent position) to a functional group that complexes, even weakly, cobalt, the organozinc compound corresponding to Ar'X may form, which may be problematic during synthesis. In general therefore, they are not used as adjuvant aromatic halide.

On the other hand, such compounds may, without an adjuvant aromatic, be easily converted into organozinc compounds.

The acid concentration is advantageously at least equal to $10^{-3}$M, advantageously $5 \times 10^{-3}$M. The upper value is essentially limited by the amount of metallic zinc in the medium. The amount of acid must be less than that needed to dissolve all of the metallic zinc and leave enough metallic zinc for the reaction.

According to the present invention, it is possible to replace in the equivalent amounts (expressed in moles) by iodine ($I_2$).

In general, whether iodine or acids, it is preferable to be at a relatively low level in order to avoid spurious reactions, especially the formation of hydrocarbon instead of the desired organozinc compound. In general therefore, amounts of acid or of iodine of less than 10%, advantageously at most equal to 5%, for the aromatic constituting the precursor substrate of the organozinc compound expressed in moles are used.

The concentration of an ArX to be converted into a zinc compound, where X represents the halide or pseudohalide of said aryl (pseudo)halide and where Ar represents the aromatic residue, is not critical. However, it is preferable to be in a concentration range lying between $10^{-2}$M and 2 M, preferably between $2 \times 10^{-2}$M and 1.5M.

The pressure is virtually of no importance in the reaction.

On the other hand, the temperature may be a factor in reducing the yield; in particular, it is preferable to have the temperature as low as possible, in general between the melting point of the reaction mixture at 100° C., advantageously at a temperature of at most 80° C. and even at most 50° C.

When the reaction rate is high enough, it is advantageous for the temperature to be close to room temperature, and even 0° C.

The substrates (ArX) that can be converted into organozinc compounds by the present invention represent a broad range of compounds. In general, the halides are halides corresponding to the relatively heavy halogens, that is to say to the halogens heavier than fluorine.

It may also be pointed out that, when the halogen (X) is linked to an aromatic ring depleted in electrons, it is preferable to use bromine or chlorine as halogen, chlorine being reserved for rings that are particularly depleted in electrons. If the condition is fulfilled by six-membered heterocycles, in the case of homocyclic aryl compounds, in order to use a chlorine it is preferable for the sum of the Hammett constants $\sigma_p$ of the substituents (not taking into account the leaving halide) to be at least equal to 0.40, preferably at least equal to 0.50. In contrast, rings that are particularly rich in electrons may use iodine as halide.

For more details about Hammett constants, the reader may refer to the $3^{rd}$ edition of the manual written by Professor Jerry March "Advanced Organic Chemistry" (pages 242 to 250) published by John Wiley and Sons.

The substrates (ArX) having, as aromatic ring carrying X, five-membered heterocycles, which include a chalcogen (such as furan and thiophene) as heteroatom, exhibit high convertibility into zinc compound, show exceptional reactivity and are always easily convertible into zinc compound.

The electron depletion of the ring may be due either to the presence of electron-withdrawing groups as substituents or, in the case of six-membered rings, by the replacement of a carbon with a heteroatom. In other words, the electron-depleted ring may be a six-membered heterocyclic ring, especially heterocyclic rings having an atom from the nitrogen column, and more particularly nitrogen.

Among electron-withdrawing groups giving good results, mention should be made of acyl groups, nitrile groups, sulfone groups, carboxylate groups, trifluoromethyl groups or, more generally, perfluoroalkyl groups and halogens of lower rank than the halide that will be converted into an organozinc compound. When the substituents are halogens of the same rank, a diorganozinc compound is generally formed.

Among donor groups, that is to say those giving mediocre results with chlorine but good results with bromine, mention may be made of alkyloxyl groups, alkyl groups and amine and dialkylamine groups.

The aromatic derivative, namely the substrate of the present method, advantageously satisfies the following formula:

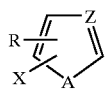

where:

Z represents a trivalent —C(R$_1$)=link, an atom of Column V, advantageously a nitrogen;

X represents the leaving halogen; and

A represents either a link chosen either from ZH groups or from chalcogens, advantageously of a rank at least equal to that of sulfur, or from two-membered divalent unsaturated groups CR$_2$=CR$_3$, N=CR$_2$ or CR$_2$=N.

If they are carried by adjacent atoms, two of the radicals R, R$_1$, R$_2$ and R$_3$ may be linked to form rings.

Thus the aryl groups may in particular be chosen from the following formulae:

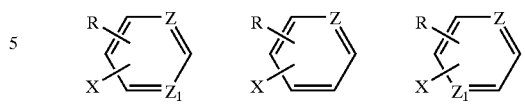

where Z$_1$ is chosen from the same meanings as those given for Z.

The radicals R$_1$, R$_2$, R$_3$ are chosen from the abovementioned substituents and especially:

electron-withdrawing groups, in particular acyl groups, nitrile groups, sulfone groups, carboxylate groups, trifluoromethyl groups or, more generally, perfluoroalkyl groups and halogens of lower rank than the halide that will be converted into an organozinc compound;

donor groups, especially aryloxyl and alkyloxyl groups, hydrocarbyl groups, such as aryl and alkyl (the latter word being taken in its etymological sense) and amine groups, including those that are monosubstituted and disubstituted with alkylamine hydrocarbon groups.

It is desirable for the substrates to have at most 50 carbon atoms, advantageously at most 30 carbon atoms and preferably at most 20 carbon atoms.

Among the substrates that are particularly useful are aryl halides, preferably aryl chlorides, or more particularly aryl bromides, especially those carrying, in the meta position, an aliphatic (i.e. sp$^3$) carbon carrying at least two fluorines, for example trifluoromethylaryl halides, preferably trifluoromethylaryl chlorides.

This method of synthesizing organozinc compounds may be extended, on the one hand, to all those in which the organozinc groups are linked to sp$^2$-hybridized carbon atoms and especially to the synthesis of organozinc compounds from vinyl halides, most particularly when these are conjugated with aromatic rings. In general, the substrate is added last to the reaction mixture.

Another subject of the present invention is a composition forming a reactant that can be used to carry out the synthesis of organozinc compounds, characterized in that it comprises a cobalt salt, a zinc salt, a polar aprotic solvent and elemental zinc in divided form, the elemental zinc being in solid form, the other elements being in a form dissolved in the solvent. This composition furthermore includes an acid or molecular iodine.

The constituents of the reactant may be added in various orders of addition.

According to a standard but nonobligatory method of implementation, the salts used (cobalt salt, if this is provided, zinc salt and optionally other salts), the adjuvants (such as iodine or acid) for activating the metallic zinc and the optional Ar'X' (or the ArX, or a portion of ArX, when there is no Ar'X') are introduced into the solvent, followed secondly by the zinc and finally by the ArX (when there is an Ar'X', or when all of the ArX has not yet been introduced).

As teaching, through the example (paradigm), the reader may refer to the general experimental conditions that give an order of introduction of the components of the reactant. These general operating conditions were used in the examples.

General Experimental Conditions:

The following mixture was initially prepared:

1) 20 ml acetonitrile solvent, or 20 ml acetonitrile +0.5 ml adiponitrile (1.5 equivalents relative to the $CoBr_2$), or 20 ml acetonitrile+MVK (1.5 equivalents relative to the $CoBr_2$)—methyl vinyl ketone (MVK) is stable under the operating conditions.

Powdered Zn: 50 mmol (3.3 eq/ArX)

$CF_3COOH$: 0.0125 to 0.025M

PhBr(Ar'X'): 0.10 eq/ArX $CoBr_2$: 0.10 eq/ArX $ZnBr_2$: 0.10 eq/ArX.

Once the release of Ar'H was over, in general ¼ of an hour after the above mixture was produced, the substrate ArX was added in an amount equal to 15 mmol.

2) ArBr: 15 mmol

Reaction:

where FG represents the substituent under investigation of the aromatic.

The following nonlimiting examples illustrate the invention.

EXAMPLE 1

Nature of the Solvent

In solvent: 20 ml $CH_3CN$

| FG | X | % ArH | % ArAr | % ArX remaining | % ArZnX |
|---|---|---|---|---|---|
| p-OCH$_3$ | Br | 10 | 4 | 9 | 78 |
| p-C$_2$H$_5$OCO | Br | 10 | 17 | 0 | 73 |
| m-CF$_3$ | Br | 6 | 10 | 0 | 84 |

In solvent: 20 ml $CH_3CN$+1.5 eq/$CoBr_2$ adiponitrile

| FG | X | % ArH | % ArAr | % ArX remaining | % ArZnX |
|---|---|---|---|---|---|
| p-OCH$_3$ | Br | 16 | 13 | 0 | 71 |
| p-C$_2$H$_5$OCO | Br | 11 | 12 | 0 | 76 |
| m-CF$_3$ | Br | 12 | 3 | 0 | 80 |
| p-CN | Br | 3 | 2 | 0 | 95 |

In solvent: 20 ml $CH_3CN$+1.5 eq/$CoBr_2$ MVK

| FG | X | % ArH | % ArAr | % ArX remaining | % ArZnX |
|---|---|---|---|---|---|
| p-OCH$_3$ | Br | 14 | 34 | 0 | 52 |
| p-C$_2$H$_5$OCO | Br | 7 | 8 | 0 | 85 |
| p-CN | Br | 5 | 0 | 0 | 95 |

The results obtained from these various solvents vary from one species to another; it was therefore chosen to work in a 20 ml $CH_3CN$+1.5 eq/$CoBr_2$ adiponitrile mixture.

EXAMPLE 2

Nature of the Halide Linked to the Zinc

With $ZnBr_2$:

| FG | X | % ArH | % ArAr | % ArX remaining | % ArZnX |
|---|---|---|---|---|---|
| p-OCN | Br | 0 | 0 | 0 | 100 |
| p-CH$_3$ | Br | 9 | 20 | | 71 |

With $ZnCl_2$:

| FG | X | % ArH | % ArAr | % ArX remaining | % ArZnX |
|---|---|---|---|---|---|
| p-OCN | Br | 0 | 0 | 0 | 100 |

With $Zn(CH_2SO_3)_2$:

| FG | X | % ArH | % ArAr | % ArX remaining | % ArZnX |
|---|---|---|---|---|---|
| p-CH$_3$ | Br | 50 | 3 | | 47 |

EXAMPLE 3

Moment of Introduction of the Zinc Salt (Here $ZnBr_2$)

In solvent: 20 ml $CH_3CN$+1.5 eq/$CoBr_2$ adiponitrile $ZnBr_2$ in the first step

| FG | X | % ArH | % ArAr | % ArX remaining | % ArZnX |
|---|---|---|---|---|---|
| p-OCH$_3$ | Br | 16 | 13 | 0 | 71 |
| m-CF$_3$ | Br | 12 | 3 | 0 | 80 |
| p-COCH$_3$ | Br | 15 | 34 | 0 | 52 |
| p-C$_2$H$_5$OCO | Br | 11 | 12 | 0 | 76 |

In solvent: 20 ml $CH_3CN$+1.5 eq/$CoBr_2$ adiponitrile $ZnBr_2$ in the second step

| FG | X | % ArH | % ArAr | % ArX remaining | % ArZnX |
|---|---|---|---|---|---|
| p-OCH$_3$ | Br | 11 | 0 | 0 | 89 |
| p-C$_2$H$_5$OCO | Br | 13 | 9 | 0 | 76 |
| p-COCH$_3$ | Br | 15 | 34 | 0 | 52 |

The results obtained are substantially the same as those obtained according to the usual procedure.

EXAMPLE 4

Nature of the Halide Linked to the Zinc

Either $ZnBr_2$ or $ZnCl_2$ is used, the results are the same: in the cases of p-BrPhCN, 100% p-BrZnPhCN was obtained in both cases.

EXAMPLE 5

Nature of the Activant for the Powdered Zinc

In solvent: 20 ml $CH_3CN$+1.5 eq/$CoBr_2$ adiponitrile Activant: $CF_3COOH$

| FG | X | % ArH | % ArAr | % ArX remaining | % ArZnX |
|---|---|---|---|---|---|
| p-OCH$_3$ | Br | 16 | 13 | 0 | 71 |
| p-C$_2$H$_5$OCO | Br | 11 | 12 | 0 | 76 |

In solvent: 20 ml CH$_3$CN+1.5 eq/CoBr$_2$ adiponitrile Activant: I$_2$

| FG | X | % ArH | % ArAr | % ArX remaining | % ArZnX |
|---|---|---|---|---|---|
| p-OCH$_3$ | Br | 12 | 0 | 0 | 88 |
| p-C$_2$H$_5$OCO | Br | 7 | 19 | 0 | 75 |

In solvent: 20 ml CH$_3$CN+1.5 eq/CoBr$_2$ adiponitrile Activant: acetic acid

| FG | X | % ArH | % ArAr | % ArX remaining | % ArZnX |
|---|---|---|---|---|---|
| p-OCH$_3$ | Br | 22 | 0 | 0 | 77 |
| p-C$_2$H$_5$OCO | Br | 16 | 14 | 0 | 70 |

If the activant is I$_2$, the zinc derivative yields are improved.

EXAMPLE 6

Replacement of PhBr with Other Aromatic Halides in the First Phase of the Reaction Whether Ar'X', p-BrPhCOOEt, p-BrPhCN, m-BrPhCF$_3$, o-BrPhCN, or 3-bromopyridine was used, results identical to those obtained with PhBr were obtained. All these halides were converted into PhH, except in the case of o-BrPhCN, which was partly converted into o-BrZnPhCN.

1) Choice of aromatic halide (Ar'Br)

Conditions: CH$_3$CN (20 ml), adiponitrile (0.5 ml), CoBr$_2$ (0.1 eq), ZnBr$_2$ (0.1 eq), CF$_3$COOH (0.0125 to 0.025M), powdered zinc (3.3 eq), Ar'Br (0.1 eq), addition of 15 mmol of ArBr (1 eq) when all the Ar'Br has been consumed. ArBr is p-BrPhOCH$_3$. The following Ar'X compounds were tested one after another: p-BrPhCO$_2$Et, p-BrPhCN, m-BrPhCF$_3$, o-BrPhCN, 3 BrPyridine.

The results obtained (p-BrZnPhOCH$_3$ yields from 65 to 72%) are similar to those obtained with PhBr. All the Ar'Br compounds were converted into ArH, except for o-BrPhCN, which was partly converted into o-BrZnPhCN.

2) Influence of the Ar'Br/CoBr$_2$ ratio

The operating conditions were the same as those of 1), with ArBr being p-BrPhOCH$_3$ and Ar'X' being PhBr. Three Ar'X'/CoBr$_2$ ratios were examined experimentally.

The Ar'Br/CoBr$_2$ ratio of ½[(0.05 eq)/(0.1 eq)] gave the same result as with a ratio of 1 [Ar'X=CoBr$_2$=0.1 eq], namely a p-BrZnPhOCH$_3$ yield ranging from 68 to 70%.

A ratio of 2 [(0.2 eq)/0.1 eq)] gave the same result. In this case however, it was established that about 50% of the PhBr was converted into PhZnBr.

EXAMPLE 7

Influence of the Presence of the Pyridine

1) Same conditions as those of example 6-1 with, as solvent, the CH$_3$CN/pyridine (20 ml/2.5 ml) mixture, without adiponitrile.

With ArBr being p-BrPhOCH$_3$ and Ar'X' being PhBr, it was observed that the reaction was greatly slowed down.

2) Same conditions as 1), but with no PhBr.

Starting from p-BrPhOCH$_3$, practically no p-BrZnPhOCH$_3$ was obtained in 24 H, whereas in the absence of pyridine the reactions lasted from 15 to 20 min.

3) Same conditions as 2) with ArBr=p-BrPhCO$_2$Et.

60% ArBr converted into p-BrZnPhCO$_2$Et in 24 H. Thus, the presence of pyridine greatly slows down the formation of organozinc compounds whose ring is rich in electrons.

EXAMPLE 8

Study of the Various Substrates

The following working conditions were chosen:
1) Solvent: 20 ml acetonitrile+0.5 ml adiponitrile
   Powdered zinc: 50 mmol (3.3 eq/Arx)
   CF$_3$COOH: (.0.0125 to 0.025M)
   PhBr(Ar'X'): 0.10 eq/ArX
   CoBr$_2$: 0.10 eq/ArX
   ZnBr$_2$: 0.10 eq/ArX.
2) ArBr: 15 mmol The reactions were carried out at room temperature. The results obtained were the following:

| FG | X | % ArH | % ArAr | % ArX remaining | % ArZnX |
|---|---|---|---|---|---|
| p-OCH$_3$ | Br | 16 | 13 | 0 | 71 |
| m-OCH$_3$ | Br | 7 | 23 | 0 | 70 |
| o-OCH$_3$ | Br | 6 | 7 | 0 | 87 |
| p-CH$_3$ | Br | 9 | 20 | 0 | 71 |
| p-C$_2$H$_5$OCO | Br | 11 | 12 | 0 | 76 |
| m-CF$_3$ | Br | 12 | 3 | 0 | 80 |
| p-Cl | Br | 6 | 5 | 0 | 89 |
| p-F | Br | 9 | 21 | 0 | 70 |
| p-COCH$_3$ | Br | 15 | 34 | 0 | 52 |
| p-CN | Br | 3 | 2 | 0 | 95 |
| m-CN | Br | 4 | 0 | 0 | 96 |
| o-CN | Br | 0 | 0 | 0 | 100 |
| 3-Bromothiophene | Br | 29 | 8 | 7 | 55 |
| 2-Bromopyridine | Br |  | 0 | 0 | 100 |
| p-CH$_3$OCO | Cl | 23 | 0 | 71 | 6 |
| p-OCH$_3$ | I | 8 | 3 | 0 | 88 |
| p-C$_2$H$_5$OCO | I | 14 | 11 | 0 | 75 |
| X—(CH$_2$)$_3$CO$_2$C$_2$H$_5$ | Br | 43 | 0 | 45 | 12 |
| X—(CH$_2$)$_3$CN | Br |  | 0 | 0 | 100 |
| X—Ph—SO$_2$ | Cl | 23 | 0 | 37 | 41 |
| p-CO$_2$CH$_3$ | Cl | 23 | 0 | 71 | 6 |
| p-NH$_2$ | Br | 52 | 0 | 8 | 40 |

*CoBr$_2$: 0.20 eq/ArX; ZnBr$_2$: 0.20 eq/ArX.

EXAMPLE 9

Split Addition of CoBr$_2$

Same conditions as in example 6 but without Ar'Br and without ArBr and CoBr$_2$=0.01 eq. The mixture was left for 30 min, then 0.09 eq of CoBr$_2$ and 1 eq of ArBr (p-BrPhCO$_2$Et) were added.

A p-BrZnPhCO$_2$Et yield of 60% (reaction yield) was obtained.

EXAMPLE 10

Two-step Reactions

Identical conditions to example 6, but in two steps:
1$^{st}$ step: no ArBr and no ZnBr$_2$
2$^{nd}$ step: after 10 to 30 minutes, ZnBr$_2$ (0.1 eq) and ArBr (1 eq) were added.
Results:

| ArBr | % ArH | % Ar—Ar | % ArZnX |
|---|---|---|---|
| p-BrPhCO$_2$Et | 13 | 8 | 76 |
| p-BrPhCOCH$_3$ | 14 | 12 | 74 |
| p-BrPhOCH$_3$ | 11 | 0 | 89 |
| p-BrPhCH$_3$ | 14 | 19 | 67 |

Results substantially the same as those obtained according to the standard procedure, except with p-BrPhCOCH$_3$ where the yield is markedly increased (74% of ArZnX in 10 minutes), but at 20° C. this zinc compound decomposes and is progressively converted into Ar—Ar.

EXAMPLE 11

Influence of the Temperature

Conditions identical to example 6, but the reactions were carried out at 0° C. and without adiponitrile.

| ArBr | % ArH | % Ar—Ar | % ArX remaining | % ArZnX | Time (min) |
|---|---|---|---|---|---|
| p-BrPhCHO | 9 | 44 | 23 | 23 | 80 |
| p-BrPhCOCH$_3$ | 8 | 23 | 10 | 59 | 25 |

In both cases, progression toward Ar—Ar when the temperature increases.

What is claimed is:

1. A process for the synthesis of aryl organozinc compounds from a reaction mixture comprising a metallic zinc and an aryl halide of the formula:

$$ArX$$

wherein Ar is an aromatic residue and X is a halogen heavier than fluorine, said process comprising the step of using cobalt as catalyst.

2. The process as claimed in claim 1, wherein the cobalt is introduced into the reaction mixture in the cobaltous state.

3. The process as claimed in claim 1, wherein the cobalt is weakly coordinated.

4. The process as claimed in claim 1, wherein the synthesis is carried out in the presence of an adjuvant aromatic halide of the formula:

$$Ar'X'$$

wherein X' represents a halogen heavier than fluorine, and Ar' represents an aromatic derivitive whose ring carrying the halogen X' is less electron-rich than the radical Ar.

5. The process as claimed in claim 4, wherein the the aromatic of formula Ar'X' is present in a content, expressed in moles per liter, is at most equal to the cobalt concentration in the reaction mixture.

6. The process as claimed in 1, wherein the reaction mixture furthermore includes an acid soluble in the mixture, or molecular iodine.

7. The process as claimed in claim 1, wherein the substrate ArX is added last.

8. The process as claimed in claim 1, wherein the halide X of ArX is bromine or iodine, advantageously bromine.

9. A composition forming a reactant that can be used to carry out the synthesis of organozinc compounds, comprising a cobalt salt, a zinc salt, a polar aprotic solvent and elemental zinc in divided form, the elemental zinc being in solid form, the other elements being in a form dissolved in the solvent.

10. The composition as claimed in claim 9, further comprising an acid or molecular iodine.

* * * * *